United States Patent [19]

Caciagli et al.

[11] Patent Number: 5,130,447
[45] Date of Patent: Jul. 14, 1992

[54] PROCESS FOR THE SYNTHESIS OF $N^\alpha$-FLUORENYLMETHOXYCARBONYL-$N^G$TRITYL-ARGININE

[75] Inventors: Valerio Caciagli; Antonio S. Verdini, both of Rome, Italy

[73] Assignee: Sclavo S.p.A., Siena, Italy

[21] Appl. No.: 706,325

[22] Filed: May 28, 1991

Related U.S. Application Data

[62] Division of Ser. No. 454,158, Dec. 21, 1989, Pat. No. 5,079,375.

[30] Foreign Application Priority Data

Dec. 23, 1988 [IT] Italy ................. 23097 A/88

[51] Int. Cl.$^5$ ............................................. C07C 129/12
[52] U.S. Cl. ..................................... 552/104; 530/337
[58] Field of Search ......................... 552/104; 530/337

[56] References Cited

U.S. PATENT DOCUMENTS 4,923,966 5/1990 Callens et al. ....................... 530/338

FOREIGN PATENT DOCUMENTS 0277561 8/1988 European Pat. Off. ............. 552/104

*Primary Examiner*—Alan L. Rotman
*Assistant Examiner*—Raymond Covington
*Attorney, Agent, or Firm*—Hedman, Gibson & Costigan

[57] ABSTRACT

An improvement is described in the synthesis method for $N^\alpha$-trityl-$N^G$-trityl arginine within a process for preparing $N^\alpha$-fluorenylmethoxycarbonyl-$N^G$-trityl-arginine from arginine, comprising:

a) forming $N^\alpha$-trityl-$N^G$-trityl-arginine
b) selectively detaching the trityl group from the $\alpha$-NH$_2$ and
c) introducing the fluorenylmethoxycarbonyl group in its place.

The improvement consists of preparing the $N^\alpha$-trityl-$N^G$-trityl-arginine by solubilizing the arginine in an aprotic organic solvent by tri-alkylsilylation both of the amino nitrogen and of the carboxyl group, followed by tritylation, with trityl chloride, of the $\alpha$-amino nitrogen, and of the guanidino group after deprotonating this latter with a bicyclic guanidine. The new improved process can also lead to variable quantities of the arginine analogue di-tritylated at the guanidino group, namely $N^\alpha$-fluorenylmethoxycarbonyl-$N^G$-di-trityl-arginine. This new compound, to which the present invention also relates, can also be used as such in peptide synthesis.

3 Claims, No Drawings

PROCESS FOR THE SYNTHESIS OF $N^\alpha$-FLUORENYLMETHOXYCARBONYL-$N^G$-TRITYL-ARGININE This is a divisional of application Ser. No. 07/454,158 filed Dec. 21, 1989, now U.S. Pat. No. 5,079,375.

This invention relates to a new synthesis method for $N^\alpha$-fluorenylmethoxycarbonyl-$N^G$-trityl-arginine, the new derivative $N^\alpha$-fluorenylmethoxcarbonyl-$N^G$-di-trityl-arginine, the process for preparing this new compound, the $N^G$-di-tritylated intermediates obtained in this process, and the use of the new compound in peptide synthesis. More particularly, a first subject of the present invention is an improved synthesis method for $N^\alpha$-fluorenylmethoxycarbonyl-$N^G$-trityl-arginine of formula (I)

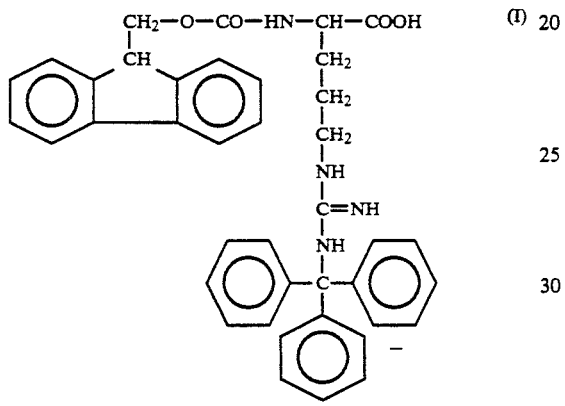

This compound, indicated for brevity as $N^\alpha$-Fmoc-$N^G$-Trt-Arg-OH, was recently described in EP No.-A-277,561. It is an arginine derivative protected at the α-amino group and at the side-chain guanidino group with orthogonal protecting groups, and has proved extremely useful in both the solution and, in particular, the solid phase synthesis of peptides containing one or more arginine residues in the sequence (thymopentin, human atrial natriuretic peptide, etc.). According to said European patent application, this compound is prepared by three successive steps, which can be indicated schematically as follows:

a) reacting the arginine with an at least double molar quantity of trityl iodide in the presence of a hydroiodic acid acceptor, to obtain $N^\alpha$-trityl-$N^G$-trityl-arginine, b) selective detritylation in the α- position of the obtained derivative by dissolving the $N^\alpha$-trityl-$N^G$-trityl-arginine hydrochloride in methanol, and c) introducing the fluorenylmethoxycarbonyl group in the α-position by reacting the $N^G$-trityl-arginine hydrochloride with a reactive derivative of fluorenylmethoxycarbonyl acid, possibly after tri-alkyl-silylation of the α-NH₂ group and the carboxyl. In this process, the second and third steps do not create excessive problems in that they proceed with satisfactory yields when using substantially conventional reactants and reaction conditions, whereas step a) not only requires the use of trityl iodide which is a reactant not commercially available, but also requires particularly balanced reaction conditions to obtain a yield which is in any event not greater than 30-35%. It has now been found possible to improve the process described in said European patent application by modifying the first step, i.e. that for preparing $N^\alpha$-trityl-$N^G$-trityl-arginine of formula (II)

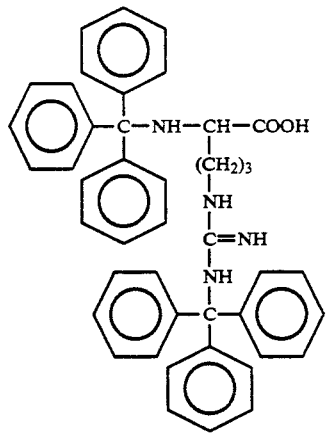

According to the present invention, this preparation is done as follows:

i) reacting arginine in an aprotic organic solvent with an at least double molar quantity of a tri-alkyl-silylating agent to obtain a homogeneous solution, and ii) alkylating the amino function in the α- position and, after deprotonation by treating with a strong non-alkylatable base of the bi-cyclic guanidine class, the side-chain guanidino function, with trityl chloride. By using a deprotonating agent as indicated, the guanidino function becomes easily tritylable and it is therefore sufficient to use trityl chloride without having to form the corresponding iodide. In addition, as the procedure can be carried out in an aprotic reaction medium, the problem of instability of the trityl chloride is overcome, this being a main obstacle in obtaining satisfactory yields in the process of EP-A-277,561. In detail, with regard to the preparation of the arginine derivative tritylated both at the α-NH₂ and at the guanidino group, the reaction is conducted in the presence of any aprotic inert solvent such as an alkyl or cyclic ether, e.g. diethyl ether, diisopropyl ether, dioxane, tetrahydrofuran, dimethoxyethane etc., a halogenated alkyl or aryl hydrocarbon, e.g. methylene chloride, chloroform, dichoroethane, chlorobenzene etc., or a mixture of these.

The silylating agent can be any known silylating agent in this field.

The trialkylchlorosilanes, such as trimethylchlorosilane or triethylchlorosilane, the bis-trialkylsilylacetamides and the trialkylsilylcyanides have proved to be particularly suitable silylating agents.

The silylating agent is used in a molar quantity of at least double that of the initial arginine, in that the solubilization of the arginine is obtained by trialkyl-silylation both of the amino nitrogen and of the carboxyl group, but because of the extreme lability of silylating agents in the presence of water, it is preferable to exceed this quantity. Generally the optimum molar ratio of silylating agent to arginine is between 2.5 and 4. If a trialkylchlorosilane is used as the silylating agent, the reaction is conducted in the presence of an organic base containing tertiary nitrogen which also acts as an acceptor for the hydrochloric acid which forms in the reaction. Suitable organic bases are the trialkylamines, and in particular triethylamine (TEA) and di-isopropylethylamine, pyridine and the alkyl-pyridines such as picoline, lutidine etc. This organic base is used in a quantity at least equimolar to the trialkylchlorosilane used, but is preferably used in excess, typically up to a 50 mol % excess.

The reaction can be conveniently carried out at ambient temperature, even though generally it is preferable to slightly heat to optimize its progress. Optimum temperatures lie between 30° and 50° C.

When a solution of the arginine tri-alkyl-silylate derivative in the chosen solvent has been obtained, tritylation of the amino nitrogen in the α-position is effected and the arginine guanidino group is deprotonated and tritylated, to obtain the derivative of formula (II).

The tritylation reaction can be effected in a single step by adding a quantity of trityl chloride at least equal to the stoichiometric quantity required by the reaction, and adding the non-alkylatable strong base necessary for deprotonation. To as far as possible prevent by-product formation, it is in any event preferable to firstly effect tritylation of the amino group in the α-position by adding an equimolar quantity or slight excess of trityl chloride and, when α-alkylation has occurred, adding the remaining trityl chloride and the non-alkylatable strong base, to obtain tritylation of the guanidino group. Whether conducted in two separate steps or in a single step, this tritylation reaction is extremely fast and is generally complete within a few hours (1-5 hours). This step can also be conducted at ambient temperature, but an optimum temperature range is typically 30°-50° C. With regard to non-alkylatable strong bases for use as deprotonating agents for the guanidino function, these are chosen from cyclic organic bases with a tertiary nitrogen atom bonded to one atom of ketoimino carbon, representable by the following general formula (III)

(III)

where $R_1$ represents an alkylene amino radical of formula $-(CH_2)_n-NR_3$, where one or more hydrogen atoms can be substituted by hydrocarbon radicals, n is between 2 and 6 and $R_3$ is a hydrocarbon radical, and $R_2$ is an alkylene radical possibly substituted as stated heretofore. Bicyclic guanidines corresponding to the aforesaid formula which can be used in the process of the invention include 7-methyl1,5,7-triazabicyclo[4.4.0]dec-5-ene, which is a commercial product. Finally, in two-step tritylation, the quantity of trityl chloride necessary for tritylation of the guanidino group must be at least equimolar to the arginine, but is preferably in excess over this quantity.

If a large excess is used, the product obtained by the tritylation is a mixture, of variable ratio depending on the extent of the excess, of arginine derivatives tritylated at the amino nitrogen in the α- position and mono- and di-tritylated at the guanidino group. If desired, this mixture can be separated into the two intermediate components, but it is also possible to carry out the subsequent steps of selective de-tritylation at the amino nitrogen and introduction of the fluorenylmethoxycarbonyl group on the mixture of these two intermediates. By carrying out these steps as described in the said European patent application, after selective de-tritylation a mixture is obtained containing $N^G$-trityl-arginine hydrochloride and $N^G$-di-trityl-arginine hydrochloride, and, on termination of the process, a mixture of $N^\alpha$-fluorenylmethoxycarbonyl-$N^G$-trityl-arginine and $N^\alpha$-fluorenylmethoxycarbonyl-$N^G$-di-trityl-arginine. This mixture is then separated into the two pure products by conventional chromatographic methods. Using the new improved method of the present invention the $N^\alpha$-Fmoc-$N^G$-Trt-Arg-OH is generally obtained in an overall yield (i.e. calculated on the initial arginine) of greater than 50%. However, the quantity of $N^\alpha$-Fmoc-$N^G$-(Trt)$_2$-Arg-OH depends on the extent of the excess of trityl chloride used in step a) of the overall process. It has also been found possible to further optimize the overall synthesis process for $N^\alpha$-fluorenylmethoxycarbonyl-$N^G$-tritylarginine and/or $N^\alpha$-fluorenylmethoxycarbonyl-$N^G$-di-trityl-arginine. In particular, it has been found that the $N^\alpha$-tritylated intermediates, i.e. both the $N^\alpha$-trityl-$N^G$-trityl-arginine and the $N^\alpha$-trityl-$N^G$-di-trityl-arginine, can be selectively detritylated at the α-amino function, as in step b) of the overall process, by simply treating with hot acetic acid. This treatment is generally conducted by dissolving the product obtained in the first step in acetic acid and keeping the obtained solution at a temperature typically between 40° and 60° C. until detritylation of the α-$NH_2$ is complete (1-2 h). On termination of the reaction the acetic acid is removed by evaporation and stripping at reduced pressure, the crude product obtained being dissolved in a small quantity of protic solvent, typically a lower alkanol such as methanol or ethanol, and the intermediate or the mixture of intermediates is then precipitated from the obtained solution by adding a non-solvent, typically an alkyl or cyclic ether. The product obtained in this manner can then be used as such in the third and last step of the overall process, i.e. the introduction of the fluorenylmethoxycarbonyl group in the α-position. In this case once the Fmoc group has been introduced to the α-$NH_2$, it is however necessary to wash with an aqueous $NH_4Cl$ solution because the acetic acid environment could have produced the acetate of the substituted guanidino group, which would result in the production of an amino acid derivative for peptide synthesis containing acetic acid. For the purposes of the overall process for the synthesis of $N^\alpha$-Fmoc-$N^G$-Trt-Arg-OH and/or $N^\alpha$-Fmoc-$N^G$-(Trt)$_2$-Arg-OH, the ability to conduct the α- detritylation under such conditions has the great advantage of making the overall process much simpler. The present invention therefore also provides a process for the synthesis of $N^\alpha$-fluorenylmethoxycarbonyl-$N^G$-trityl-arginine and/or $N^\alpha$-fluorenylmethoxycarbonyl-$N^G$-di-trityl-arginine comprising a) forming the $N^\alpha$-trityl-$N^G$-trityl-arginine and/or $N^\alpha$-trityl-$N^G$-di-trityl-arginine, b) selectively detaching the trityl group from the α-$NH_2$, and c) introducing the fluorenylmethoxycarbonyl group in its place, characterised in that step b) is effected by treatment with hot acetic acid.

Not only $N^\alpha$-Fmoc-$N^G$-Trt-Arg-OH but also $N^\alpha$-Fmoc-$N^G$-(Trt)$_2$-Arg-OH has proved useful in the synthesis of peptides containing arginine residues.

The present invention therefore further provides the new arginine derivative, namely $N^\alpha$-fluorenylmethoxycarbonyl-$N^G$-di-trityl-arginine, which is useful as an intermediate in the solution or solid phase synthesis of peptides containing at least one arginine unit in the sequence. This is typically introduced using the strategy of the active ester which is formed in situ by treatment with an excess of HOBt in the presence of a carbodiimide (DCCI. DIPCI). Because of the complete protection provided by the presence of two trityl groups in the side chain, the peptide can be prolonged using either the active ester strategy or the symmetrical anhydride strategy. In contrast to the $N^\alpha$-Fmoc-$N^G$-Trt-Arg-OH, for which the side chain protecting group is removed on termination of the peptide synthesis by trifluoroacetic acid in the presence of suitable scavengers, when using $N^\alpha$-Fmoc-$N^G$-(Trt)$_2$-Arg-OH it is necessary to use a mixture of trifluoroacetic acid and concentrated hydrochloric acid to deprotect the guanidino group. As already seen, this new derivative can be obtained by a threestep process comprising:

A) preparing the $N^\alpha$-trityl-$N^G$-di-trityl-arginine or a mixture of $N^\alpha$-trityl-$N^G$-di-trityl-arginine and $N^\alpha$-trityl-$N^G$-trityl-arginine by reacting arginine in an aprotic organic solvent with a trialkyl-silylating agent to obtain a solution, then alkylating the amino function in the $\alpha$-position, and, after deprotonation by treatment with a non-alkylatable strong acid of the bicyclic guanidine class, alkylating the guanidino function in the side chain, with an excess of trityl chloride, B) selective $\alpha$ de-tritylation of the derivative or mixture of derivatives obtained in this manner (with hydrochloric acid or with hot acetic acid), and C) introducing the fluorenylmethoxycarbonyl in the $\alpha$-position by reacting with a reactive derivative of fluorenylmethoxycarbonyl acid after possible tri-alkyl-silylation of the $\alpha$-amino and carboxyl functions. With regard to step A), the aforesaid is valid in relation to the preparation of the $N^\alpha$-fluorenylmethoxycarbonyl-$N^G$-trityl-arginine, using for tritylation of the guanidino group an excess of trityl chloride over the starting arginine. However, with regard to steps B) and C), use can be made of the procedure described in EP-A-277,561, the contents of which are incorporated into this patent application for reference, and with regard to step B) the aforesaid procedure can be used, The present invention finally provides the new $N^G$-di-tritylated intermediates obtained in the synthesis process for the $N^\alpha$-fluorenylmethoxycarbonyl-$N^G$-trityl-arginine, i.e. the $N^\alpha$-trityl-$N^G$-di-trityl-arginine and the $N^G$-di-trityl-arginine hydrochloride. It should finally be noted that the fact of having identified extremely mild conditions for the de-tritylation of the $\alpha$-NH$_2$ (hot acetic acid) makes it possible to consider for some peptide syntheses the direct use of the $N^\alpha$-trityl-$N^G$-trityl-arginine and/or $N^\alpha$-trityl-$N^G$-di-trityl-arginine intermediates (i.e. without passing to the corresponding $N^\alpha$-fluorenylmethoxycarbonyl derivatives). In this respect, such a use is possible when the protecting groups present in the already formed peptide chain, i.e. that to which the arginine residue is to be bound, are stable in the presence of hot acetic acid, such conditions being extremely mild, even if acid. The purpose of the following examples is merely to better illustrate the process of the present invention, the new $N^\alpha$-fluorenylmethoxycarbonyl-$N^G$-di-trityl-arginine derivative, and the new $N^G$-di-tritylated derivatives.

EXAMPLE 1

Preparation of
$N^\alpha$-fluorenylmethoxycarbonyl-$N^G$-trityl-argine
($N^\alpha$-Fmoc-$N^G$-Trt-Arg-OH)

a) A mixture of arginine (1.74 g, 10 mmoles) and trimethylchlorosilane (TMSC) (3.8 ml, 30 mmoles) in methylene chloride (60 ml) is heated under reflux for 30 minutes. Triethylamine (5.55 ml, 40 mmoles) is then added and the mixture further heated under reflux until a homogeneous solution is obtained. Commercial trityl chloride (2.78 g, 10 mmoles) is added to the mixture and heating is continued for a further 30 minutes. TLC analysis on E$_{254}$ Kieselgel 60 silica gel plates, eluting with an 85/10/5 chloroform/methanol/acetic acid mixture) shows nearly total conversion of the initial arginine into $N^\alpha$-trityl-arginine. Trityl chloride (5.56 g, 20 mmoles) and 7-methyl-1,5,7-triazabicyclo[4.4.0]dec-5-ene (MTBD) (5.5 ml, 35.9 mmoles) are added to the reaction solution, maintaining the reflux. A further two portions of MTBD (2.75 ml, 18 mmoles each) are added 10 and 60 minutes after the initial MTBD addition, and heating under reflux is continued for a further 3 hours. After cooling to ambient temperature the solution is acidified with a ⅛ (v/v) acetic acid/methylene chloride mixture. Ethyl ether is added to the organic phase until it is lighter than the water, after which it is washed abundantly with water (6×100 ml), with a 5% aqueous NaHCO$_3$ solution (50 ml) and again with water (2×50 ml). The organic phase is dried over Na$_2$SO$_4$, filtered and evaporated to dryness in a rotary evaporator, to obtain a spongy solid (9.6 g).

b) This crude product is dissolved in ethyl ether (1000 ml) containing tetrahydrofuran (35 ml) and precipitated as the hydrochloride by adding under strong stirring a solution of HCl (30 mmoles) in anhydrous ethyl ether (100 ml). The precipitate is collected by filtration and de-tritylated for 2 hours in methanol at ambient temperature. Ethyl ether is added to the methanolic solution and the white precipitate which forms is recovered by filtration, and washed with ethyl ether to give a crude product (6.75 g) which is found, on reverse-phase HPLC analysis [Column: Lichrosorb RP18 (10µ) (25×0.4 cm i.d.); Eluent: A=CH$_3$CN, 0.1% TFA; B=H$_2$O, 0.1% TFA; Gradient: from 37% to 80% of A in B in 20 minutes; Flow: 1.5 ml/min] to contain two compounds with a retention time of 3.89 and 14.55 minutes. The first product, which constitutes most of the mixture, co-elutes with an authentic sample of $N^G$-Trt-Arg-OH, while the second product is analyzed in FAB-MS to show a strong MH$^+$ signal of m/z 659 corresponding to the protonated molecular ion of $N^G$-(Trt)$_2$-Arg-OH. The structure of this second product is thus confirmed by classical analysis methods.

c) The mixture of these two products is placed in tetrahydrofuran (400 ml), and N,O-bis-(trimethylsilyl)-acetamide (BSA) (10 ml, 41 mmoles) added. Keeping the mixture under strong stirring, complete solubilization is obtained after 40 minutes. The solution is then cooled to 0° C. and fluorenylmethoxycarbonyl chloride (FmocCl) (2.58 g, 10 mmoles) in tetrahydrofuran (50 ml) is added drop by drop over a period of 30 minutes under strong stirring. On termination of the reaction methanol is added, the mixture is evaporated to dryness and the residue obtained is taken up in a small quantity of a 9/1 (v/v) methylene chloride/methanol mixture and analyzed by HPLC under the conditions indicated above. At 230 nm the sample under examination reveals the complete disappearance of peaks at 3.89 and 14.55 minutes and the appearance of three peaks at 16.26, 18.51 and 25.86 minutes. At 301 nm (wavelength which detects only the Fmoc group) the sample shows three peaks at the same retention times as the analysis at 230 nm, of which the first, which co-elutes with an authentic sample of $N^\alpha$-Fmoc-$N^G$-Trt-Arg-OH, represents 60.4% of the initial moles of FmocCl (and thus an overall $N^\alpha$-Fmoc-$N^G$-Trt-Arg-OH yield of 60.4% calculated on the starting arginine). The second peak, which co-elutes with an authentic sample of FmocCl, represents 20.8% in relation to the initial quantity of FmocCl. The third peak, which as then confirmed by $^1$H-NMR analysis consists of $N^\alpha$-Fmoc-$N^G$-(Trt)$_2$-Arg-OH, represents 18.7% of the visible signals and thus a yield of 18.7 on the starting arginine. The pure compounds are then isolated from the reaction mixture by chromatography in a silica gel column (55 cm × 6 cm i.d.; 70–230 mesh) eluting with 9/1 (v/v) methylene chloride/methanol, with a flow of 2 ml/min. After discarding the first three fractions (for a total of 0.5 liters), the next six fractions (or a total of about 1 liter) are evaporated to dryness and re-chromatographed under the same conditions, to recover $N^\alpha$-fluorenylmethoxycarbonyl-$N^G$-ditrityl-arginine (1.39 g; M.P. 152°–4° C.), and a further 2 liters are discarded, enabling $N^\alpha$-fluorenylmethoxycarbonyl-$N^G$-trityl-arginine (3.9 g) to be collected from the tail fractions. The $^1$H-NMR spectra, which in the case of $N^\alpha$-Fmoc-$N^G$-Trt-Arg-OH coincides with that reported in EP-A-277,561, confirm the assigned structures. The characteristic peaks of $N^\alpha$-Fmoc-$N^G$-(Trt)$_2$-Arg-OH in DMSO-d$_6$ are as follows ($\delta$, TMS): 6.75–7.90 (41H, trityl, Fmoc, $\alpha$-NH, guanidino), 4.15–4.20 (3H, CH$_2$O, CH, Fmoc), 3.70 (m, 1H, $\alpha$-Arg), 3.18 (m, 2H,$\delta$-Arg), 0.90–1.40 (4H, $\beta$, $\gamma$-Arg).

On treatment with a 9/1 (v/v) trifluoroacetic acid/HCl (37%) mixture for 30 minutes, the $N^\alpha$-Fmoc-$N^G$-(Trt)$_2$-Arg-OH gives a product which, under the HPLC conditions indicated heretofore, co-elutes with an authentic sample $N^\alpha$-Fmoc-Arg-OH. The compound is however completely stable in pure trifluoroacetic acid. This stability allows extremely versatile use of $N^\alpha$-Fmoc-$N^G$-(Trt)$_2$-Arg-OH in the solid-phase synthesis of peptides containing one or more arginine units in sequence. These can be effected either with the Fmoc-amino acid strategy or with the t-Boc-amino acid strategy.

EXAMPLE 2 b) The crude reaction product obtained in step a) of Example 1 is dissolved in acetic acid (AcOH) (50 ml) and kept at 50° C. for 1 h. The AcOH is then removed by evaporation under vacuum (1 mmHg) and the residue is taken up and evaporated several times with toluene until all the AcOH has been removed. The residue obtained is taken up in McOH (30 ml) and precipitated by adding Et$_2$O (300 ml) drop by drop under strong stirring. The crude precipitate obtained in this manner (3.6 g) is shown by reverse-phase HPLC analysis [Column: Lichrosorb RP18 (10$\mu$) (25 × 0.4 cm i.d.); Eluent: A=CH$_3$CN, 0.1% TFA; B=H$_2$O, 0.1% TFA; Gradient: from 37% to 80% of A in B in 20 minutes; Flow: 1.5 ml/min] to contain two compounds with a retention time of 3.89 and 14.55 minutes. The first product, which constitutes most of the mixture, co-elutes with an authentic sample of $N^\epsilon$-Trt-Arg-OH, while the second co-elutes with an authentic sample of $N^G$-(Trt)$_2$-Arg-OH.

c) The mixture of these two products is placed in tetrahydrofuran and BSA (10 ml, 41 mmoles) is added. The mixture is kept under strong stirring for 40 minutes, after which a solution of FmocCl (2.58 g, 10 mmoles) in tetrahydrofuran is added drop by drop over a period of 7 minutes under strong stirring and at room temperature. Methanol (50 ml) is then added, the mixture is evaporated to dryness and the residue obtained is taken up in EtOAc, washed with a 5% solution of NH$_4$Cl (3 × 50 ml) and finally with H$_2$O (3 × 50 ml). The organic phase is then dried over Na$_2$SO$_4$ and evaporated to dryness. The residue obtained is taken up in a small quantity of a 9/1 (v/v) methylene chloride/methanol mixture and analyzed by HPLC under the aforesaid conditions. At 230 nm the sample under examination reveals the complete disappearance of peaks at 3.89 and 14.55 minutes and the appearance of three peaks at 16.26, 18.51 and 25,86 minutes. At 301 nm (wavelength which detects only the Fmoc group) the sample shows three peaks at the same retention times as the analysis at 230 nm, of which the first, which coelutes with an authentic sample of $N^\alpha$-Fmoc-$N^G$-Trt-Arg-OH, represents 50.5% of the initial moles of FmocCl (and thus an overall $N^\alpha$-Fmoc-$N^G$-(Trt)$_2$-Arg-OH yield of 50.5% calculated on the starting arginine). The FmocCl and the $N^\alpha$-Fmoc-$N^G$-(Trt)$_2$-Arg-OH, represented respectively 22% and 12% of the reaction mixture, the rest of the signals visible at 301 nm representing FmocOH and other impurities. They are then isolated by silica gel chromatorgraphy as described in the preceding example. The analytical data for the products obtained in this manner correspond to those reported in EP-A-277561 and in the preceding example.

EXAMPLE 3

The two arginine derivatives obtained in Example 1 are used in the solid phase synthesis of the di-peptide H-Arg-Phe-OH using a polydimethylacrylamide support in accordance with the Sheppard method, with activation by HOBt/DCCI for the two arginine derivatives, and with the suitable unblocking methods heretofore described. The two crude reaction products from the two preparations are analyzed by HPLC for ionic coupling at 259 nm [Column: Nucleosil 5C18 (25 cm × 4.6 cm i.d.); Eluent: A=CH$_3$CN, 0.1% TFA; B=H$_2$O, PIC 5 × 10$^{-3}$M, 0.1% TFA; Gradient: from 10% to 40% of A in B in 30 minutes; Flow: 0.7 ml/min]. After comparing the elution profiles with that of a mixture (1:1) of the H-DArg-LPhe-OH and H-LArg-LPhe-OH diastereoisomers prepared by another method and which under these conditions were perfectly separate, analysis showed the presence of H-DArg-L-Phe-OH in a quantity less than 0.1%.

EXAMPLE 4

Use of the compound $N^\alpha$-Fmoc-$N^G$-(Trt)$_2$-Arg-OH in the synthesis of thymopentin The procedure described in EP-A-277,561 is substantially followed, except that $N^\alpha$-Fmoc-$N^G$-(Trt)$_2$-Arg-OH is used for introducing the arginine, preparing its active ester of 1-hydroxybenzotriazole in situ as described in the said patent application. On termination of the synthesis, instead of using trifluoracetic acid containing 10% of ethanedithiol as the unblocking agent, a mixture of trifluoroacetic acid (17.5 ml), 37% hydrochloric acid (1.5 ml) and ethanedithiol (1 ml) is used. The peptide separation and purification are then effected as therein described, the yield calculated on the first amino acid residue incorporated being 77%.

We claim:

1. A method for the selective removal of a trityl group from the $\alpha$-amino group of a compound chosen from $N^\alpha$-trityl-$N^G$-trityl-arginine and $N^\alpha$-trityl-$N^G$-di-trityl-arginine and mixtures thereof, consisting of treating said compound with acetic acid at a temperature of between about 40° C. and about 60° C.

2. The compound $N^\alpha$-fluorenylmethoxycarbonyl-$N^G$-di-trityl-arginine.

3. $N^\alpha$-trityl-$N^G$-di-trityl-arginine, and $N^G$-di-trityl-arginine hydrochloride.

* * * * *